United States Patent [19]

Hart

[11] Patent Number: 4,698,363

[45] Date of Patent: Oct. 6, 1987

[54] PROSTACYCLIN ANALOGUES

[75] Inventor: Terance W. Hart, Essex, England

[73] Assignee: May & Baker Limited, Essex, England

[21] Appl. No.: 799,796

[22] Filed: Nov. 20, 1985

[30] Foreign Application Priority Data

Nov. 22, 1984 [GB] United Kingdom ............... 8429545

[51] Int. Cl.$^4$ .................. C07C 177/00; A61K 31/557
[52] U.S. Cl. ................................. 514/530; 514/573;
536/46; 560/53; 560/56; 560/116; 560/119;
562/462; 562/466; 562/498; 562/501
[58] Field of Search ............. 562/501, 498, 462, 466;
560/919, 116, 53, 56; 536/46; 514/530, 573

[56] References Cited

U.S. PATENT DOCUMENTS

| 4,192,891 | 3/1980 | Haslanger | 560/119 |
|---|---|---|---|
| 4,517,202 | 5/1985 | Bird | 514/530 |

FOREIGN PATENT DOCUMENTS

| 0134153 | 3/1985 | European Pat. Off. | 560/119 |
|---|---|---|---|
| 0136779 | 4/1985 | European Pat. Off. | 560/119 |
| 0171992 | 2/1986 | European Pat. Off. | 560/119 |
| 110539 | 7/1983 | Japan | 562/501 |
| 59-210044 | 11/1984 | Japan | 560/119 |
| 60-028943 | 2/1985 | Japan | 560/119 |
| 139645 | 7/1985 | Japan | 562/501 |
| 60-202840 | 10/1985 | Japan | 560/119 |
| 61-030549 | 2/1986 | Japan | 560/119 |
| 61-085346 | 4/1986 | Japan | 560/119 |
| 61-085348 | 4/1986 | Japan | 560/119 |
| 84/02902 | 8/1984 | PCT Int'l Appl. | 560/119 |
| 86/02923 | 5/1986 | PCT Int'l Appl. | 562/501 |

Primary Examiner—Robert Gerstl
Attorney, Agent, or Firm—Stevens, Davis, Miller & Mosher

[57] ABSTRACT

Prostaglandin analogues of the formula:

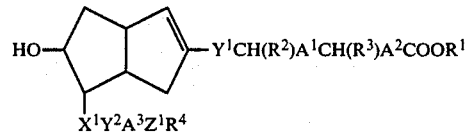

II (wherein $R^1$ represents a hydrogen atom or an aliphatic or alicyclic hydrocarbon radical, $Y^1$ represents a carbonyl or hydroxymethylene group, $A^1$ represents an alkylene linkage containing 1, 2 or 3 carbon atoms and optionally bearing a methyl or ethyl substituent, $R^2$ represents a hydrogen atom or a methyl or ethyl group and $R^3$ represents a hydrogen atom or $R^2$ and $R^3$ form an alkylene linkage containing 2 or 3 carbon atoms, optionally bearing a methyl or ethyl substituent, such that the symbols $A^1$, $R^2$ and $R^3$, together with the carbon atoms through which they are connected, may form a cycloalkyl ring of 5, 6, 7 or 8 carbon atoms, optionally bearing one or two methyl or ethyl substituents, or $A^1$ and $R^3$, together with the carbon atom through which they are connected, may form a phenylene ring optionally substituted by a halogen atom or by a trifluoromethyl group or by a straight- or branched-chain alkyl or alkoxy group containing from 1 to 6 carbon atoms, $A^2$ represents a direct bond or a methylene group optionally bearing one or two methyl or ethyl substituents, $X^1$ represents an ethylene, transvinylene or ethynylene group, $Y^2$ represents a carbonyl or hydroxymethylene group, and either (i) $A^3$ represents a straight- or branched-alkylene chain containing from 1 to 5 carbon atoms, $Z^1$ represents a direct bond or an oxygen or sulphur atom, and $R^4$ represents a group $R^{4'}$ which is an aliphatic or alicyclic hydrocarbon radical, or $R^4$ represents a phenyl group optionally substituted by a halogen atom or by a trifluoromethyl group or by a straight- or branched-chain alkyl or alkoxy group containing from 1 to 6 carbon atoms, or (ii) $A^3$ and $Z^1$ both represent direct bonds and $R^4$ represents a group $R^{4'}$ as hereinbefore defined) and cyclodextrin clathrates thereof and non-toxic salts thereof possess useful pharmacological properties.

23 Claims, No Drawings

PROSTACYCLIN ANALOGUES

DESCRIPTION

This invention relates to new prostaglandin $I_2$ analogues, to processes for their preparation, to pharmaceutical compositions containing them, and to key intermediates which can be used in their preparation.

Prostaglandin $I_2$ (otherwise known as $PGI_2$ or prostacyclin) is a physiologically active natural substance having the formula shown in FIG. I of the drawings assembled at the end of this specification and its chemical name is (5Z,13E)-(9S,11R,15S)-6,9-epoxy-11,15-dihydroxyprosta-5,13-dienoic acid [Nature, 263, 663 (1976), Prostaglandins, 12, 685 (1976), ibid, 12, 915 (1976), ibid, 13, 3 (1977), ibid, 13, 375 (1977) and Chemical and Engineering News, Dec. 20, 17 (1976).

It is well known that $PGI_2$ can be prepared by incubation of prostaglandin $G_2$ ($PGG_2$) or prostaglandin $H_2$ ($PGH_2$) with microsomal fractions prepared from thoracic aorta of swine, mesenteric artery of swine, rabbit aorta or the stomach fundus of rats. $PGI_2$ has a strong relaxing activity on the artery and some other kinds of smooth muscle. Furthermore, $PGI_2$ strongly inhibits arachidonic acid-induced blood platelet aggregation of the human.

Taking into consideration that thromboxane $A_2$, prepared by incubation of $PGG_2$ or $PGH_2$ with blood platelet microsome, has a contracting activity on the artery and an aggregating activity on blood platelets, the properties of $PGI_2$ heretofore mentioned show that $PGI_2$ fulfils a very important physiological part in a living body. $PGI_2$ may be useful in the treatment of arteriosclerosis, atherosclerosis, cardiac failure, thrombosis, hypertension, angina or asthma.

Natural $PGI_2$ is so unstable (being deactivated in a buffer solution at pH 7.6 after 20 minutes at 22° C., or after 10 minutes at 37° C.) that application of $PGI_2$ for medical purposes is difficult.

Widespread investigations have been carried out in order to discover processes for the chemical preparation of more stable analogues of $PGI_2$, and their products possessing the pharmacological properties of the 'natural' $PGI_2$ or one or more of such properties to an enhanced degree, or hitherto unknown pharmacological properties. As a result of extensive research and experimentation it has been discovered that in certain analogues of $PGI_2$ and derivatives thereof the properties of the 'natural' $PGI_2$ are, in some aspects of its activities, improved or modified.

The present invention accordingly provides new prostaglandin analogues of the general formula shown in FIG. II [wherein $R^1$ represents a hydrogen atom or an aliphatic or alicyclic hydrocarbon radical, for example a straight- or branched-chain alkyl group containing from 1 to 12, more particularly 1 to 6, carbon atoms, optionally substituted by a cycloalkyl group containing from 3 to 8 carbon atoms, or a mono-, bi- or tri-cycloalkyl or mono-, bi- or tri-cycloalkenyl group containing up to 10 carbon atoms and optionally substituted by one or two straight- or branched-chain alkyl or alkenyl groups each containing up to 3 carbon atoms, e.g. a cyclohexyl or a 6,6-dimethylbicyclo[3,1,1]hept-2-en-2-yl group, $Y^1$ represents a carbonyl or hydroxymethylene group, $A^1$ represents an alkylene linkage containing 1, 2 or 3 carbon atoms and optionally bearing a methyl or ethyl substituent, $R^2$ represents a hydrogen atom or a methyl or ethyl group and $R^3$ represents a hydrogen atom or $R^2$ and $R^3$ form an alkylene linkage containing 2 or 3 carbon atoms, optionally bearing a methyl or ethyl substituent, such that the symbols $A^1$, $R^2$ and $R^3$, together with the carbon atoms through which they are connected, may form a cycloalkyl ring of 5, 6, 7 or 8 carbon atoms, optionally bearing one or two methyl or ethyl substituents, or $A^1$ and $R^3$, together with the carbon atom through which they are connected, may form a phenylene ring optionally substituted by a halogen (e.g. chlorine, bromine, fluorine or iodine) atom or by a trifluoromethyl group or by a straight- or branched-chain alkyl or alkoxy group containing from 1 to 6 carbon atoms, $A^2$ represents a direct bond or a methylene group optionally bearing one or two methyl or ethyl substituents, $X^1$ represents an ethylene, trans-vinylene or ethynylene group, $Y^2$ represents a carbonyl or hydroxymethylene group, and either (i) $A^3$ represents a straight- or branched-alkylene chain containing from 1 to 5 carbon atoms, $Z^1$ represents a direct bond or an oxygen or sulphur atom, and $R^4$ represents a group $R^{4'}$ which is an aliphatic or alicyclic hydrocarbon radical, for example a straight- or branched-chain alkyl group containing from 1 to 12 carbon atoms, optionally substituted by a cycloalkyl group containing from 3 to 8 carbon atoms, or a mono-, bi- or tri-cycloalkyl or mono-, bi- or tri-cycloalkenyl group containing up to 10 carbon atoms and optionally substituted by one or two straight- or branched-chain alkyl or alkenyl groups each containing up to 3 carbon atoms, e.g. a cyclohexyl or a 6,6-dimethylbicyclo[3,1,1]hept-2-en-2-yl group, or $R^4$ represents a phenyl group optionally substituted by a halogen (e.g. chlorine, bromine, fluorine or iodine) atom or by a trifluoromethyl group or by a straight- or branched-chain alkyl or alkoxy group containing from 1 to 6 carbon atoms, or (ii) $A^3$ and $Z^1$ both represent direct bonds and $R^4$ represents a group $R^{4'}$ as hereinbefore defined] as well as the cyclodextrin clathrates and, when $R^1$ represents a hydrogen atom, non-toxic salts thereof.

In this specification, whenever reference is made to compounds of the formula shown in FIG. II, it is intended to refer also to the said cyclodextrin clathrates and non-toxic salts thereof whenever the context so permits.

As will be apparent to those skilled in the art, the compounds of the formula shown in FIG. II have at least four centres of chirality, these four centres of chirality being at the carbon atoms in positions 8, 9, 11 and 12. In addition to these four centres of chirality, a further centre of chirality will occur when $Y^1$ or $Y^2$ represents a hydroxymethylene group and still further centres of chirality may occur in the groups $A^3$, $R^1$ and $R^4$ and in the group $—CH(R^2)A^1CH(R^3)A^2—$. The presence of centres of chirality, as is well known, leads to the existence of isomerism. However, the compounds of the formula shown in FIG. 11 all have such a configuration that the hydrogen atoms attached to the bridgehead carbon atom in positions 8 and 9 are cis with respect to each other. Accordingly, all isomers of the formula shown in FIG. 11, and mixtures thereof, which have those hydrogen atoms, attached to the bridgehead carbon atoms in positions 8 and 9, in the cis-configuration are within the scope of the present invention. Preferably the hydrogen atoms attached to the 8 and 9 positions are in the same configurations as those in $PGI_2$, viz. beta and beta respectively. Particularly preferred compounds are those wherein the side-chain attached in the 12-position is cis with respect to the said hydrogen atoms attached to the bridgehead carbon atoms in positions 8 and 9, and those compounds wherein the hydroxy group attached in the 11-position is trans with respect to the side-chain attached in the 12-position.

Compounds of the formula shown in FIG. 11 which are of especial importance are those of the general formula shown in FIG. III (wherein $A^1$, $A^2$, $A^3$, $R^1$, $R^2$, $R^3$, $R^4$, $X^1$, $Y^1$, $Y^2$ and $Z^1$ are as hereinbefore defined) and also their enantiomers and non-toxic salts and cyclodextrin clathrates thereof.

Especially preferred classes of compounds of the formula shown in FIG. II are those which exhibit one or more of the following features:

(i) $A^1$ represents a methylene group;
(ii) $A^2$ represents a direct bond;
(iii) $A^3$ represents a direct bond;
(iv) $R^1$ represents an alkyl group containing from 1 to 6 carbon atoms or a cyclohexyl group;
(v) $R^2$ represents a hydrogen atom;
(vi) $R^3$ represents a hydrogen atom;
(vii) $R^4$ represents an alkyl group containing from 1 to 5 carbon atoms or a cyclohexyl group;
(viii) $X^1$ represents an ethynylene group;
(ix) $Y^2$ represents a hydroxymethylene group; and/or
(x) $Z^1$ represents a direct bond; other symbols being as hereinbefore defined Individual compounds of particular importance include the following:

| | |
|---|---|
| methyl (9S,11R,15S)-15-cyclohexyl-11,15-dihydroxy-6,9-methano-5-oxo-16,17,18,19,20-pentanor-prost-6,6a-en-13-ynoate and its (9R,11S,15S)-diastereoisomer; | A |
| (±)-methyl (9S,11R),[mixture of 15R and 15S]-11,15-dihydroxy-6,9-methano-5-oxoprost-6,6a-en-13-ynoate; | B |
| (±)-methyl (9S,11R),[mixture of 5R and 5S],-[mixture of 15R and 15S]-5,11,15-trihydroxy-6,9-methanoprost-6,6a-en-13-ynoate; | C |
| hexyl (9S,11R,15S)-15-cyclohexyl-11,15-dihydroxy-6,9-methano-5-oxo-16,17,18,19,20-pentanor-prost-6,6a-en-13-ynoate and its (9R,11S,15S)-diastereoisomer; | D |
| isopropyl (9S,11R,15S)-15-cyclohexyl-11,15-dihydroxy-6,9-methano-5-oxo-16,17,18,19,20-pentanor-prost-6,6a-en-13-ynoate and its (9R,11S,15S)-diastereoisomer; and | E |
| cyclohexyl (9S,11R,15S)-15-cyclohexyl-11,15-dihydroxy-6,9-methano-5-oxo-16,17,18,19,20-pentanor-prost-6,6a-en-13-ynoate and its (9R,11S,15S)-diastereoisomer. | F |

The letters A to F are assigned to the compounds for easy reference later in the specification.

The compounds of the formula shown in FIG. II and cyclodextrin clathrates and non-toxic salts thereof possess valuable pharmacological properties, for example, properties typical of the related series of natural products known as prostaglandins.

In laboratory tests, the compounds reduced diastolic blood pressure in rates (anaesthetised with pentobarbitone) when administered intravenously at doses as shown in Table I below, which indicates the dose required in mg/kg animal body weight to produce a 25% fall in diastolic blood pressure ($ED_{25}$).

TABLE I

| Test Compound | $ED_{25}$ mg/kg |
|---|---|
| A | 0.0036 |
|   | 0.0052 |
| B | 0.0384 |

TABLE I-continued

| Test Compound | $ED_{25}$ mg/kg |
|---|---|
| C | greater than 0.5 |
| D | 0.0217 |
| E | 0.0172 |
| F | 0.0046 |

These results are indicative of utility in the prevention or treatment of conditions such as hypertension and cardiac conditions such as angina and myocardial infarction.

Furthermore, compounds of the formula shown in FIG. II have utility in the prevention or treatment of cerebral conditions such as brain anoxia.

In tests, mice were treated subcutaneously with test compound and, 30 minutes later, they were subjected to a hypoxic gas mixture (4% $O_2$; 96% $N_2$). The survival rate given below in Table II is a measure of the number of mice found to survive for a statistically significant period after mice in a control group.

TABLE II

| Test Compound | Dose mg/kg animal body weight | Survival rate (%) |
|---|---|---|
| A | 1.0 | 90 |
| B | 1.0 | 70 |
| D | 1.0 | 80 |
| E | 1.0 | 80 |
| F | 1.0 | 90 |
| $PGI_2$ methyl ester | 0.3 | 45 |

In further tests compounds of formula II, for example compound A at oral doses of 0.1 and 0.3 mg/kg animal body weight, gave significant inhibition of indomethacin-induced gastric ulceration in the rat.

These results are indicative of utility in the prevention or treatment of conditions such as gastrointestinal bleeding induced by non-steroidal anti-inflammatory drugs, and peptic ulceration.

Further tests indicate that compounds of formula II inhibit blood platelet aggregation. For example, compound A gave 50% inhibition of rabbit blood platelets in vitro at concentrations of 0.14, 0.09, 0.08, 0.06 and 0.08 mg/l.

These results are indicative of utility in the treatment or prevention of thromboses.

These utilities are enhanced by the fact that the compounds of the formula shown in FIG. II are far more stable than natural $PGI_2$ and so they and their pharmaceutical compositions may be manipulated, stored and administered relatively easily.

According to a feature of the present invention, compounds of the formula shown in FIG. II wherein $Y^2$ represents a hydroxymethylene group are prepared by the acid hydrolysis of compounds of the general formula shown in FIG. IV wherein $A^1$, $A^2$, $A^3$, $R^1$, $R^2$, $R^3$, $R^4$, $X^1$, $Y^1$ and $Z^1$ are as hereinbefore defined and $R^5$ represents a suitable acid-labile protecting group.

This process is particularly applicable to the preparation of compounds of the formula shown in FIG. II wherein $R^1$ represents an aliphatic or alicyclic hydrocarbon radical, $X^1$ represents a trans-vinylene or ethynylene group, $Y^1$ represents a carbonyl group, and $Y^2$ represents a hydroxymethylene group, that is to say the preparation of compounds of the general formula shown in FIG. V (wherein $A^1$, $A^2$, $A^3$, $R^2$, $R^3$, $R^4$ and $Z^1$ are as hereinbefore defined, $X^2$ represents a transvinylene or ethynylene group, and R⁶ represents a group within the definition of $R^1$ other than a hydrogen atom, by the acid hydrolysis of compounds of the general formula shown in FIG. VI (wherein $A^1$, $A^2$, $A^3$, $R^2$, $R^3$, $R^4$, $R^5$, $R^6$, $X^2$ and $Z^1$ are as hereinbefore defined), within the formula shown in FIG. IV.

Hydrolysis of compounds of the formula shown in FIG. IV is generally effected in mild acidic conditions, for example by treatment with an aqueous inorganic acid, e.g. dilute hydrochloric acid or a catalytic quantity of perchloric acid, or an aqueous organic acid, for example aqueous acetic acid, e.g. 50-80% v/v aqueous acetic acid, preferably in the presence of an inert organic solvent, for example a lower alkanol, e.g. ethanol, or an ether, e.g. diethyl ether or tetrahydrofuran, and optionally in the presence of a cation exchange resin, e.g. Dowex $AG_{50}W—X8$ H+ resin. The hydrolysis is generally carried out at temperatures from 0° C. to 100° C.; when dilute hydrochloric acid is used, at from 40° to 80° C., preferably from 50° to 60° C.; when a catalytic quantity of perchloric acid is used, at from 0° to 40° C., preferably from 15° to 25° C.; and when aqueous acetic acid is used, at from 0° to 80° C., preferably from 35° to 50° C.

Suitable acid labile protecting groups represented by $R^5$ are those which are easily removed by acid hydrolysis and which do not cause side reactions, e.g. a 2-tetrahydropyranyl group unsubstituted or substituted by at least one straight- or branched-chain alkyl group containing from 1 to 4 carbon atoms, or a 2-tetrahydrofuranyl group, or a tert-butyldiphenylsilyl group, or a trialkylsilyl group of the general formula:

$—SiR^7R^8R^9$       VII (wherein $R^8$ and $R^9$, which may be the same or different, each represents a methyl or ethyl group and $R^7$ represents a straight- or branched-chain alkyl group containing from 1 to 4 carbon atoms), e.g. a trimethylsilyl, triethylsilyl, dimethylisopropylsilyl or tert-butyldimethylsilyl group, or a 1-alkoxyalkyl group of the general formula:

$—CH(CH_2R^{10})OR^{11}$       VIII (wherein $R^{10}$ represents a hydrogen atom or a straight- or branched-chain alkyl group containing from 1 to 4 carbon atoms and $R^{11}$ represents a straight- or branched-chain alkyl group containing from 1 to 4 carbon atoms) e.g. a 1-ethoxyethyl group.

Preferably $R^5$ represents a tert-butyldimethylsilyl or triethylsilyl group.

As an alternative feature of the present invention, compounds of the formula shown in FIG. IV wherein $A^1$, $A^2$, $A^3$, $R^1$, $R^2$, $R^3$, $R^4$, $X^1$, $Y^1$ and $Z^1$ are as hereinbefore defined and $R^5$ represents a group of formula VII wherein $R^7$, $R^8$ and $R^9$ are as hereinbefore defined are converted to corresponding compounds of the formula shown in FIG. II by treatment with a quaternary ammonium fluoride, preferably tetrabutylammonium fluoride, preferably in tetrahydrofuran and preferably at or near the ambient temperature, followed by treatment with water. This process is particularly applicable to the preparation of compounds of formula II wherein $X^1$ represents an ethynylene group, the other symbols being as hereinbefore defined. The water in this process is sometimes conveniently provided by the silica gel adsorbent used in a chromatography procedure, if the reaction mixture (optionally after concentration in vacuo) is subjected to chromatography, thus effecting hydrolysis and purification in one operation.

Compounds of the formula shown in FIG. II may be prepared from other compounds of the formula shown in FIG. II. Thus, according to a further feature of the present invention, the compounds of the formula shown in FIG. V are converted to compounds of the formula shown in FIG. II, wherein $A^1$, $A^2$, $A^3$, $R^1$, $R^2$, $R^3$, $R^4$, $X^1$, $Y^1$, $Y^2$ and $Z^1$ are as hereinbefore defined but wherein one or more of the symbols $R^1$, $X^1$, $Y^1$ and $Y^2$ have the following significances:

(a) $R^1$ represents a hydrogen atom;
(b) $X^1$ represents a trans-vinylene or ethylene group;
(c) $Y^1$ represents a hydroxymethylene group;
(d) $Y^2$ represents a carbonyl group;

or to salts of compounds of the formula shown in FIG. II wherein $R^1$ represents a hydrogen atom, or to cyclodextrin clathrates of the compounds of the formula shown in FIG. II, by the application or adaptation of one or more known methods of preparing acids from esters, of preparing alcohols from ketones, of preparing ketones from alcohols, of reducing carbon-carbon triple or double bonds, of preparing salts from acids, or of preparing cyclodextrin clathrates. Furthermore, esters of the formula shown in FIG. II wherein $R^1$ represents an aliphatic or alicyclic hydrocarbon radical can be prepared by the esterification of corresponding carboxylic acids of the formula shown in FIG. II wherein $R^1$ represents a hydrogen atom.

Thus, (1) compounds of the formula shown in FIG. II in which $R^1$ represents a hydrogen atom may be prepared by the hydrolysis of the corresponding compounds of the formula shown in FIG. II wherein $R^1$ represents an aliphatic or alicyclic hydrocarbon radical by hydrolysis, for example with an aqueous alkali (e.g. lithium hydroxide, sodium hydroxide or potassium hydroxide), followed by treatment with dilute acid, e.g. hydrochloric acid, to generate the desired carboxylic acid product from the solution of alkali metal salt produced thereby.

(2) Compounds of the formula shown in FIG. II wherein $X^1$ represents an ethylene group and/or one or both of $Y^1$ and $Y^2$ represents a hydroxymethylene group (hereinafter referred to as "compounds of formula IIa") are prepared by the reduction of compounds of the formula shown in FIG. II wherein $X^1$ represents a vinylene group and/or one or both of $Y^1$ and $Y^2$ represents a carbonyl group (hereinafter referred to as "compounds of formula IIb"). Thus:

(2) (a) Compounds of formula IIa wherein one or both of $Y^1$ and $Y^2$ represents a hydroxymethylene group are prepared by reduction of the corresponding compounds of formula IIb wherein one or both of $Y^1$ or $Y^2$ represents a carbonyl group, using means and conditions capable of reducing carbonyl groups to hydroxymethylene groups without affecting carbon-carbon multiple bonds. The reduction is preferably effected by a metal borohydride or a metal alkylborohydride (e.g. sodium borohydride or potassium borohydride or lithium tri-sec-butylborohydride), usually in an aqueous, alcoholic or aqueous alcoholic medium and at between −40° and +30° C., preferably between −5° and +15° C., optionally in the presence of a base, for example an alkali metal hydroxide (e.g. aqueous sodium hydroxide or aqueous potassium hydroxide) when a metal borohydride is employed or, especially when potassium borohydride is employed, in aqueous or aqueous alcoholic conditions buffered at a pH of from pH 7 to pH 9, e.g. at pH 8 (e.g. by the addition of aqueous citric acid solution), or, when a metal alkylborohydride is employed, in an ethereal medium (e.g. tetrahydrofuran) at between $-78°$ and $0°$ C.

Alternatively the reduction is carried out by reaction with aluminium isopropoxide, in the presence of isopropanol, preferably as the solvent medium, at an elevated temperature, advantageously at the reflux temperature of the reaction mixture.

(2) (b) Compounds of formula IIa wherein $X^1$ represents an ethylene group and $Y^1$ and $Y^2$ each represents a carbonyl or hydroxymethylene group are prepared by reduction of the corresponding compounds of formula IIb wherein $X^1$ represents a vinylene group and $Y^1$ and $Y^2$ each represents a carbonyl or hydroxymethylene group, with means and in conditions capable of reducing carbon-carbon double bonds without affecting carbonyl groups. The reduction is preferably effected by hydrogenation in the presence of a hydrogenation catalyst, for example rhodium on charcoal, in the presence of an inert organic solvent, for example a lower alkanol, e.g. ethanol, generally at ambient temperature and elevated pressure, e.g. at a hydrogen pressure of 15 kilograms per square centimeter.

(2) (c) Compounds of formula IIa wherein $X^1$ represents an ethylene group and $Y^1$ and $Y^2$ both represent hydroxymethylene groups are prepared by reduction of corresponding compounds of formula IIb with means and in conditions capable of reducing any carbonyl groups represent to hydroxymethylene groups and any vinylene groups present to ethylene groups. The reduction is preferably effected by hydrogenation in the presence of a hydrogenation catalyst, for example palladium on charcoal, in the presence of an inert organic solvent, for example a lower alkanol, e.g. ethanol, preferably at an elevated pressure, e.g. at a hydrogen pressure of 15 kilograms per square centimeter.

(3) Compounds of the formula shown in FIG. II wherein one or both of $Y^1$ and $Y^2$ represents a carbonyl group may be prepared by oxidation of the corresponding compounds of the formula shown in FIG. II wherein one or both of $Y^1$ and $Y^2$ represents a hydroxymethylene group with means and in conditions capable of oxidising hydroxymethylene groups to form carbonyl groups without affecting the rest of the molecule. The oxidation is preferably effected by means of pyridinium chlorochromate, preferably in dichloromethane, or by means of pyridinium dichromate, preferably in dimethylformamide or dichloromethane, at or near room temperature, or by means of a solution prepared from chromium trioxide, sulphuric acid and water, preferably in the presence of acetone and at or below room temperature.

(4) By the term "non-toxic salts" is meant salts the cations of which are relatively innocuous to the animal organism when used in therapeutic doses so that the beneficial properties of the parent compound of the formula shown in FIG. II are not vitiated by side-effects ascribable to those cations. Preferably, the salts are water-soluble. Suitable salts include the alkali metal, e.g. sodium or potassium, and ammonium salts and pharmaceutically-acceptable (i.e. non-toxic) amine salts.

Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from alkyl groups containing from 1 to 6 carbon atoms, hydroxyalkyl groups containing 2 or 3 carbon atoms, cycloalkyl groups containing from 3 to 6 carbon atoms, phenyl groups, phenylalkyl groups containing from 7 to 11 carbon atoms and phenylalkyl groups containing from 7 to 15 carbon atoms wherein the alkyl moieties are substituted by hydroxy groups. The phenyl groups and phenyl moieties of such phenylalkyl groups may be unsubstituted or substituted by one or two alkyl groups containing from 1 to 6 carbon atoms. Suitable amines also include those derived in theory by the replacement of two of the hydrogen atoms of ammonia by a hydrocarbon chain, which may be interrupted by nitrogen, oxygen or sulphur atoms, to form, together with the nitrogen atom of ammonia to which its terminal groups are attached, a five- or six-membered nitrogen-containing heterocyclic ring, which heterocyclic ring may be unsubstituted or substituted by one or two alkyl groups containing from 1 to 6 carbon atoms. Examples of suitable amine cations include mono-, di- and tri-methylammonium, mono-, di-and tri-ethylammonium, mono-, di- and tri-propylammonium, mono-, di- and tri-isopropylammonium, ethyldimethylammonium, mono-, bis- and tris-(2-hydroxyethyl)ammonium, ethylbis(2-hydroxyethyl)ammonium, butylmono-(2-hydroxyethyl)ammonium, tris(hydroxymethyl)methylammonium, cyclohexylammonium, benzylammonium, benzyldimethylammonium, dibenzylammonium, phenyl-2-hydroxyethylammonium, piperidinium, morpholinium, pyrrolidinium, piperazinium, 1-methylpiperidinium, 4-ethylmorpholinium, 1-isopropyrrolidinium, 1,4-dimethylpiperazinium, 1-butylpiperidinium, 2-methylpiperidinium and 1-ethyl-2-methylpiperidinium.

The non-toxic salts may be prepared from parent compounds of the formula shown in FIG. II by known methods, for example by reaction of compounds of the formula shown in FIG. II (wherein $R^1$ represents a hydrogen atom) and the appropriate base, e.g. an alkali metal hydroxide or carbonate, ammonia or an amine, in a suitable solvent which is preferably water in the case of the preparation of alkali metal salts and water or isopropanol in the case of amine salts. The salts may be isolated by lyophilisation of the solution or, if sufficiently insoluble in the reaction medium, by filtration, if necessary after removal of part of the solvent.

As well as being useful in themselves as pharmaceutically useful compounds, salts of the compounds of the formula shown in FIG. II wherein $R^1$ represents a hydrogen atom are useful for the purpose of purification of the parent acids of the formula shown in FIG. II, for example by exploitation of the solubility differences between the salts and the parent acids in water and in organic solvents, by techniques well known to those skilled in the art. The parent acids of the formula shown in FIG. II can be regenerated from their salts by known methods, for example by treatment with a mineral acid, e.g. dilute hydrochloric acid.

(5) Cyclodextrin clathrates of the prostaglandin analogues of the formula shown in FIG. II may be prepared by dissolving the cyclodextrin in water or an organic solvent which is miscible with water, in the presence of triethylamine, and adding to the solution the prostaglandin analogue in a water-miscible organic solvent. The mixture is then heated and the desired cyclodextrin clathrate product isolated by concentrating the mixture under reduced pressure or by cooling and separating the product by filtration or decantation. The ratio of organic solvent to water may be varied according to the solubilities of the starting materials and products. Preferably the temperature is not allowed to exceed 70° C. during the preparation of the cyclodextrin clathrates. α-, β- or γ-Cyclodextrins or mixtures thereof may be used in the preparation of the cyclodextrin clathrates. Conversion into their cyclodextrin clathrates serves to increase the stability of the prostaglandin analogues.

(6) Compounds of the formula shown in FIG. II wherein $R^1$ represents an aliphatic or alicyclic hydrocarbon radical may be prepared by the reaction of a corresponding carboxylic acid of the formula shown in FIG. II in which $R^1$ represents a hydrogen atom with an alcohol of the general formula:

$$R^6OH \qquad\qquad IX$$

(wherein $R^6$ is as hereinbefore defined), an excess of which may be employed as solvent medium, in the presence of an inorganic acid, e.g. hydrochloric acid or sulphuric acid, preferably at a temperature between 50° and 160° C., and advantageously at the reflux temperature of the reaction mixture, or, where $R^6$ can be represented by the formula $-CHR^{12}R^{13}$ [wherein the symbols $R^{12}$ and $R^{13}$ are identical or different and each represents an alkyl group (the total number of carbon atoms in the two groups $R^{12}$ and $R^{13}$ being preferably at most 11) or, preferably, a hydrogen atom], with a diazoalkane of the general formula:

$$R^{12}R^{13}C=N_2 \qquad\qquad X$$

(wherein $R^{12}$ and $R^{13}$ are as hereinbefore defined) in an inert organic solvent medium, preferably a dialkyl ether (e.g. diethyl ether), preferably at ambient temperature. Alternatively, a silver salt of such a carboxylic acid of the formula shown in FIG. II can be reacted with an alkyl halide of the general formula:

$$R^6Z^2 \qquad\qquad XI$$

wherein $Z^2$ represents a halogen atom and $R^6$ is as hereinbefore defined, optionally in the presence of an inert organic solvent such as an aromatic hydrocarbon (e.g. benzene) at an elevated temperature and advantageously at the reflux temperature of the reaction mixture, or a sodium salt of a said carboxylic acid of the formula shown in FIG. II can be reacted with a said alkyl halide in a polar solvent, such as hexamethylphosphotriamide, preferably at room temperature.

By the term "known methods" as used in this specification is meant methods heretofore used or described in the literature.

As will be readily appreciated by those skilled in the art, the compounds of the formula shown in FIG. II, including their isomers arising from the aforementioned centres of chirality, may be separated by the application or adaptation of known methods, For example, diastereoisomeric forms may be separated by chromatography using selective adsorption from solution or from the vapour phase onto suitable adsorbents, and enantiomeric forms of compounds of the formula shown in FIG. II wherein $R^1$ represents a hydrogen atom may be separated by formation of salts with an optically active base, followed by separation of the obtained pair of diastereoisomers by, for example, fractional crystallisation from a suitable solvent system, followed by separate regeneration of the enantiomeric acids.

Compounds of the formula shown in FIG. IV may be prepared by the application or adaptation of known methods, for example methods illustrated in the description in the following Reference Examples for the preparation of compounds of the formula shown in FIG. VI.

The following Examples illustrate the preparation of the compounds of the present invention, and the Reference Examples illustrate the preparation of the intermediate compounds of the formula shown in FIG. VI.

The compounds prepared in the Examples and Reference Examples contain various centres of chirality and the products are mixtures of all possible diastereoisomers unless otherwise specified, and each one is accompanied by an equal quantity of its enantiomer. However, the two hydrogen atoms attached to the bridgehead carbon atoms in the bicyclooctane rings are always cis with respect to each other. According to the convention customarily employed, and with the structures laid out as in the formula drawings, the said hydrogen atoms attached to the bridgehead carbon atoms are said to be in the β-configuration, and the side-chain attached in the 12-position is cis with respect to the said hydrogen atoms when the said side-chain is said to be in the β-configuration. The designation (±) indicates that such compounds are accompanied by equal quantities of their enantiomers.

EXAMPLE 1

Compound A

A mixture (1:1 w/w) of 2,β-(3-cyclohexyl-3α-tert-butyldimethylsilyloxyprop-1-ynyl)-3α-tert-butyl-dimethylsilyloxy-7-(4-methoxycarbonyl-1-oxobutyl)bicyclo[3,3,0]oct-6-ene and 2α-(3-cyclohexyl-3α-tert-butyl-dimethylsilyloxyprop-1-ynyl)-3β-tert-butyl-dimethylsilyloxy-7-(4-methoxycarbonyl-1-oxobutyl)bicyclo[3,3,-0]oct-6-ene, that is to say methyl (9S,11R,15S)-11,15-bis(tert-butyldimethylsilyloxy)-15-cyclohexyl-6,9-methano-5-oxo-16,17,18,19,20-pentanorprost-6,6a-en-13-ynoate and its (9R,11S,15S)-diastereoisomer, (6.0 mg; prepared as described in Reference Example 1) was dissolved in tetrahydrofuran (0.1 ml) and treated with a solution of tetrabutylammonium fluoride in tetrahydrofuran (1.0M; 0.05 ml) at 20° C. under an argon atmosphere. The solution was stirred for 4 hours, and it was then treated with saturated aqueous ammonium chloride solution (5 ml) followed by ethyl acetate (5 ml). The organic layer was removed and the aqueous layer was extracted with ethyl acetate (2×5 ml). The organic layers were combined, washed with saturated aqueous sodium chloride solution (5 ml), dried over sodium sulphate and concentrated under reduced pressure to give an oil (4.2 mg), which was then subjected to medium pressure chromatography on a short column of silica gel, eluting with ethyl acetate, to give a mixture (1:1 w/w) of 2β-(3-cyclohexyl-3α-hydroxy-prop-1-ynyl)-3α-hydroxy-7-(4-methoxycarbonyl-1-oxo-butyl)-bicyclo[3,3,0]oct-6-ene and 2α-(3-cyclohexyl-3α-hydroxyprop-1-ynyl)-3β-hydroxy-7-(4-methoxycarbonyl-1-oxobutyl)bicyclo[3,3,0]oct-6-ene, that is to say methyl (9S,11R,15S)-15-cyclohexyl-11,15-dihydroxy-6,9-methano-5-oxo-16,17,18,19,20-pentanorprost-6,6a-en-13-ynoate and its (9R,11S,15S)-diastereoisomer, (4.0 mg) [N.M.R. (in deuterochloroform): singlet at 3.66 ppm, multiplets at 0.8-2.1, 2.2-2.5, 2.5-2.8, 3.2-3.4, 3.95-4.2, 6.45-6.62 ppm].

EXAMPLE 2

Compound B

±-2β-[(Mixture of 3α and 3β)-tert-butyldimethyl-silyloxyoct-1-ynyl]-3α-tert-butyldimethylsilyl-oxy-7-(4-methoxycarbonyl-1-oxobutyl)bicyclo[3,3,0]oct-6-ene, that is to say (±)-methyl (9S,11R),[mixture of 15R and 15S]-11,15-bis(tert-butyldimethylsilyloxy)-6,9-methano-5-oxoprost-6,6a-en-13-ynoate (27 mg; prepared as described in Reference Example 2) was treated with a solution of glacial acetic acid, water and tetrahydrofuran (2 ml; 13:7:2 v/v) and the mixture was stirred at 20° C. for 16 hours and then at 45° C. for 2 hours. The mixture was then concentrated under reduced pressure to give a crude oil (19 mg), which was subjected to medium pressure chromatography on a short column of silica gel, eluting with a mixture of ethyl acetate and hexane (1:1 v/v), to give (±)-2β-[(Mixture of 3α and 3β)-hydroxyoct-1-ynyl]-3α-hydroxy-7-(4-methoxycarbonyl-1-oxobutyl)bicyclo-[3,3,0]oct-6-ene, that is to say (±)-methyl (9S,11R),[mixture of 15R and 15S]-11,15-dihydroxy-6,9-methano-5-oxo-prost-6,6a-en-13-ynoate, (7.1 mg) [N.M.R. (in deuterochloroform): singlet at 3.7 ppm, multiplets at 0.8–1.0, 1.1–1.6, 1.6–1.8, 1.8–2.1, 2.1–2.9, 3.2–3.4, 3.95–4.15, 4.3–4.45, 6.55–6.65 ppm].

EXAMPLE 3

Compound C

A stirred solution of (±)-2β-[(mixture of 3α and 3β)-hydroxyoct-1-ynyl]-3αhydroxy-7-(4-methoxy-carbonyl-1-oxobutyl)bicyclo[3,3,0]oct-6-ene, that is to say (±)-methyl (9S,11R),[mixture of 15R and 15S]-11,15-dihydroxy-6,9-methano-5-oxo-prost-6,6a-en-13-ynoate, (4.3 mg; prepared as described in Example 2) in tetrahydrofuran (0.3 ml) at −78° C. under argon was treated with a solution of lithium tri-sec-butyl-borohydride in tetrahydrofuran (1.0M; 0.034 ml). After 90 minutes at −78° C. the reaction mixture was treated with methanol (0.03 ml) followed by hydrogen peroxide (30%; 0.03 ml). The mixture was then treated with ethyl acetate (5 ml) and saturated aqueous ammonium chloride solution (5 ml). The organic layer was removed and the aqueous layer was extracted with ethyl acetate (2×5 ml). The organic layers were combined, washed with water (5 ml), and then with saturated aqueous sodium chloride solution (5 ml), dried over sodium sulphate and concentrated under reduced pressure to give a crude oil (4 mg), which was then subjected to medium pressure chromatography on a short column of silica gel, eluting with ethyl acetate, to give (±) -2β-[(mixture of 3α and 3β)-hydroxyoct-1-ynyl]-3α-hydroxy-7-[(mixture of 1α and 1β)-hydroxy-4-methoxycarbonylbutyl)bicyclo[3,3,0]oct-6-ene, that is to say (±)-methyl (9S,11R),[mixture of 5R and 5S],-[mixture of 15R and 15S]-5,11,15-trihydroxy-6,9-methanoprost-6,6a-en-13-ynoate, (2.6 mg) [N.M.R. (in deuterochloroform): singlet at 3.68 ppm, multiplets at 0.8–1.0, 1.0–2.7, 2.4–2.55, 3.0–3.2, 3.8–4.1, 4.1–4.3, 4.3–4.5, 5.5–5.55 ppm].

EXAMPLE 4

Compound D

A mixture (1:1 w/w) of 2β-(3-cyclohexyl-3αtert-butyldimethylsilyloxyprop-1-ynyl)-3α-tert-butyl-dimethylsilyloxy-7-(4-hexyloxycarbonyl-1-oxobutyl)bicyclo[3,3,0]oct-6-ene and 2α-(3-cyclohexyl-3α-tert-butyl-dimethylsilyloxyprop-1-ynyl)-3β-tert-butyl-dimethylsilyloxy-7-(4-hexyloxycarbonyl-1-oxobutyl)bicyclo[3,3,0]oct-6-ene, that is to say hexyl (9S,11R,15S)-11,15-bis(tert-butyldimethylsilyloxy)-15-cyclohexyl-6,9-methano-5-oxō-16,17,18,19,20-pentanorprost-6,6a-en-13-ynoate and its (9R,11S,15S)-diastereoisomer, (8.3 mg; prepared as described in Reference Example 3) was dissolved in tetrahydrofuran (0.3 ml) and treated with a solution of tetrabutylammonium fluoride in tetrahydrofuran (1.0M; 0.06 ml) and stirred for 1.4 hours at 20° C. under an argon atmosphere. The reaction mixture was concentrated under reduced pressure and the residue was then subjected to medium pressure chromatography on a short column of silica gel, eluting with a mixture of ethyl acetate and hexane (1:1 v/v) and then with ethyl acetate, to give a mixture (1:1 w/w) of 2β-(3-cyclohexyl-3αhydroxyprop-1-ynyl)-3αhydroxy-7-(4-hexyloxy-carbonyl-1-oxobutyl)bicyclo[3,3,0]oct-6-ene and 2α-(3-cyclohexyl-3α-hydroxyprop-1-ynyl)-3β-hydroxy-7-(4-hexyloxycarbonyl-1-oxobutyl)bicyclo[3,3,0]oct-6-ene, that is to say hexyl (9S,11R,15S)-15-cyclohexyl-11,15-dihydroxy-6,9-methano-5-oxo-16,17,18,19,20-pentanor-prost-6,6a-en-13-ynoate and its (9R,11S,15S)diastereoisomer, (2.4 mg).

EXAMPLE 5

Compound E

A mixture (1:1 w/w) of 2β-(3-cyclohexyl-3α-tert-butyldimethylsilyloxyprop-1-ynyl)-3α-tert-butyl-dimethylsilyloxy-7-(4-isopropoxycarbonyl-1-oxobutyl)bicyclo[3,3,0]oct-6-ene and 2α-(3-cyclohexyl-3α-tert-butyl-dimethylsilyloxyprop-1-ynyl)-3β-tert-butyl-dimethylsilyloxy-7-(4-isopropoxycarbonyl-1-oxobutyl)bicyclo[3,3,0]oct-6-ene, that is to say isopropyl (9S,11R,15S)-11,15-bis(tert-butyldimethylsilyloxy)-15-cyclohexyl-6,9-methano-5-oxo-16,17,18,19,20-pentanor-prost-6,6a-en-13-ynoate and its (9R,11S,15S)-diastereoisomer, (10.5 mg; prepared as described in Reference Example 3) was dissolved in tetrahydrofuran (0.35 ml) and treated with a solution of tetrabutylammonium fluoride in tetrahydrofuran (1.0M; 0.13 ml) and stirred for 4 hours at 20° C. under an argon atmosphere. The reaction mixture was concentrated under reduced pressure and the residue was then subjected to medium pressure chromatography on a short column of silica gel, eluting with a mixture of ethyl acetate and hexane (1:1 v/v) and then with ethyl acetate, to give a mixture (1:1 w/w) of 2β-(3-cyclohexyl-3α-hydroxyprop-1-ynyl)-3α-hydroxy-7-(4-isoprop-oxycarbonyl-1-oxobutyl)bicyclo[3,3,0]oct-6-ene and 2α-(3-cyclohexyl-3α-hydroxyprop-1-ynyl)-3β-hydroxy-7-(4-isopropoxycarbonyl-1-oxobutyl)bicyclo[3,3,0]oct-6-ene, that is to say isopropyl (9S,11R,15S)-15-cyclohexyl-11,15-dihydroxy-6,9-methano-5-oxo-16,17,18,19,20-pentanor-prost-6,6a-en-13-ynoate and its (9R,11S,15S)-diastereoisomer, (3.5 mg).

EXAMPLE 6

Compound F

A mixture (1:1 w/w) of 2β-(3-cyclohexyl-3α-tert-butyldimethylsilyloxyprop-1-ynyl)-3α-tert-butyl-dimethylsilyloxy-7-(4-cyclohexyloxycarbonyl-1-oxobutyl)-bicyclo[3,3,0]oct-6-ene and 2α-(3-cyclohexyl-3α-tert-butyldimethylsilyloxyprop-1-ynyl)-3β-tert-butyldimethylsilyloxy-7-(4-cyclohexyloxycarbonyl-1-oxo-butyl)-bicyclo[3,3,0]oct-6-ene, that is to say cyclohexyl (9S,11R,15S)-11,15-bis(tert-butyldimethyl-silyloxy)-15-cyclohexyl-6,9-methano-5-oxo-16,17,18,-19,20-pentanorprost-6,6a-en-13-ynoate and its (9R,11S,15S)-diastereoisomer, (7.4 mg; prepared as described in Reference Example 3) was dissolved in tetrahydrofuran (0.3 ml) and the stirred solution was treated with a solution of tetrabutylammonium fluoride in tetrahydrofuran (1.0M; 0.086 ml) and stirred for 4 hours at 20° C. under an argon atmosphere. The reaction mixture was concentrated under reduced pressure and the residue was then subjected to medium pressure chromatography on a short column of silica gel, eluting with a mixture of ethyl acetate and hexane (1:1 v/v) and then with ethyl acetate, to give a mixture (1:1 w/w) of 2β-(3-cyclohexyl-3α-hydroxyprop-1-ynyl)-3α-hydroxy-7-(4-cyclohexyloxycarbonyl-1-oxobutyl)bicyclo[3,3,0]oct-6-ene and 2α-(3-cyclohexyl-3α-hydroxyprop-1-ynyl)-3β-hydroxy-7-(4-cyclohexyloxy-carbonyl-1-oxobutyl)-bicyclo[3,3,0]oct-6-ene, that is to say cyclohexyl (9S,11R,15S)-15-cyclohexyl-11,15-dihydroxy-6,9-methano-5-oxo-16,17,18,19,20-pentanorprost-6,6a-en-13-ynoate and its (9R,11S,15S)-diastereoisomer, (1.2 mg).

REFERENCE EXAMPLE 1

A stirred solution of a mixture (1:1 w/w) of 3α-tert-butyldimethylsilyloxy-2β-(3α-tert-butyl-dimethyl-silyloxy-3-cyclohexylprop-1-ynyl)bicyclo[3,3,0]octan-6-one and 3β-tert-butyldimethylsilyloxy-2α-(3α-tert-butyldimethylsilyloxy-3-cyclohexylprop-1-ynyl)bicyclo[3,3,0]octan-6-one (36 mg) in anhydrous tetrahydrofuran (1.0 ml) at −78° C. under an argon atmosphere was treated with a solution of lithium bis(trimethylsilyl)amide in tetrahydrofuran (1.0M; 0.06 ml) dropwise during 2 minutes. The solution was stirred for 20 minutes at −78° C. and then it was treated dropwise with a solution of 4-methoxycarbonylbutanal (28.5 mg) in tetrahydrofuran (0.3 ml). The mixture was stirred for a further period of 90 minutes at −78° C., and then it was treated with a solution of glacial acetic acid (0.01 ml) in diethyl ether (0.5 ml) and then the mixture was allowed to warm to room temperature. It was then treated with saturated aqueous ammonium chloride solution (2 ml) and extracted with ethyl acetate (2×10ml). The organic layers were combined, washed with saturated aqueous sodium chloride solution, dried over sodium sulphate and concentrated under reduced pressure to give a crude oil (46.6 mg).

This oil was then dissolved in dimethylformamide (0.2 ml) and treated with imidazole (18 mg) and then with chlorotriethylsilane (20 mg). The mixture was allowed to stand for 18 hours at 20° C. and then it was treated with hexane (10 ml) followed by water (10 ml). The organic layer was removed and the aqueous layer was extracted with hexane (2×5 ml). The organic layers were combined, washed with water (5 ml) and then with saturated aqueous sodium chloride solution, dried over sodium sulphate and concentrated under reduced pressure to give a crude oil (54.9 mg).

This oil was dissolved in a mixture of methanol (1.0 ml) and tetrahydrofuran (0.9 ml) under argon. The stirred solution was cooled to −30° C. and treated with sodium borohydride (8 mg) in one portion. After 20 minutes the solution was allowed to warm to −10° C. during 40 minutes. The solution was then treated with saturated aqueous ammonium chloride solution (10 ml) and extracted with ethyl acetate (4×5 ml). The organic layers were combined, washed with saturated aqueous sodium chloride solution, dried over sodium sulphate and concentrated under reduced pressure to give a viscous oil (53.1 mg).

This oil was dissolved in benzene (1.0 ml) and treated with triethylamine (9.3 mg) followed by methanesulphonyl chloride (10.5 mg) at 20° C. The solution was stirred at 20° C. for a further period of 2 hours, and then it was treated with saturated aqueous ammonium chloride solution and extracted with ethyl acetate (3×4 ml). The organic layers were combined, washed with saturated aqueous sodium chloride solution, dried over sodium sulphate and concentrated under reduced pressure to give an oil (61.8 mg).

A portion (53 mg) of this oil was dissolved in acetone (2 ml) and the stirred solution was treated at −30° C. with a solution of Jones' reagent (0.1 ml; "Reagents for Organic Synthesis", Fieser & Fieser, pages 142–143). After 30 minutes at −30° C. the solution was warmed to −10° C. After a further period of 3 hours at −10° C. the solution was treated with propan-2-ol (0.5 ml) and then, after 5 minutes at −10° C., with hexane (10 ml), saturated aqueous sodium chloride solution (10 ml) and saturated aqueous sodium bicarbonate solution (1 ml). The organic layer was removed and the aqueous layer was extracted with hexane (2×5 ml). The organic layers were combined, washed with saturated aqueous sodium chloride solution (5ml), dried over sodium sulphate and concentrated under reduced pressure to give a crude oil (40 mg), which was then subjected to medium pressure chromatography on a short column of silica gel, eluting with a mixture of ethyl acetate and hexane (1:6 v/v), to give a mixture (1:1 w/w) of 3α-tert-butyldimethylsilyloxy-2β-(3α-tert-butyldimethyl-silyloxy-3-cyclohexylprop-1-ynyl)-6α-methanesulphonyloxy-7-(4-methoxycarbonyl-1-oxobutyl)bicyclo[3,3,0]octane and 3β-tert-butyldimethylsilyloxy-2α-(3α-tert-butyldimethylsilyloxy-3-cyclohexylprop-1-ynyl)-6β-methanesulphonyloxy-7-(4-methoxycarbonyl-1-oxobutyl)bicyclo[3,3,0]octane (7.5 mg) [Mass spectrum m/e 643 (M+- tert-butyl)].

A stirred solution of this material in benzene (0.8 ml) was treated with 1,8-diazabicyclo[5,4,0]undec-7-ene (10 mg) at 20° C. under argon. After stirring for 20 hours at 20° C. the mixture was treated with water (10 ml) and ethyl acetate (10 ml). The organic layer was removed and the aqueous layer was extracted with ethyl acetate (3×5 ml). The organic layers were combined, washed with saturated aqueous sodium bicarbonate solution (10 ml) and then with saturated aqueous sodium chloride solution (10 ml), dried over sodium sulphate and concentrated under reduced pressure to give a mixture (1:1 w/w) of 2β-(3-cyclohexyl-3α-tert-butyldimethyl-silyloxyprop-1-ynyl)-3α-tert-butyldimethylsilyloxy-7-(4-methoxycarbonyl-1-oxobutyl)bicyclo[3,3,0]oct-6-ene and 2α.(3-cyclohexyl-3α-tert-butyldimethylsilyloxyprop-1-ynyl)-3,β-tert-butyldimethylsilyloxy-7-(4-methoxycarbonyl-1-oxobutyl)bicyclo[3,3,0]oct-6-ene, that is to say methyl (9S,11R,15S)-11,15-bis(tert-butyl-dimethylsilyloxy)-15-cyclohexyl-6,9-methano-5-oxo-16,17,18,19,20-pentanorprost-6,6a-en-13-ynoate and its (9R,11S,15S)-diastereoisomer, (6.0 mg), in the form of an oil.

REFERENCE EXAMPLE 2

By proceeding in a manner similar to that described in Reference Example 1, but using the appropriate quantity of (±)-3α-tert-butyldimethyl-silyloxy-2β-[(mixture of 3α and 3β)-tert-butyldimethyl-silyloxyoct-1-ynyl]bicyclo[3,3,0]octan-6-one as the starting material, there was prepared (±)-2β-[(mixture of 3α and 3β)-tert-butyldimethyl-silyloxyoct-1-ynyl]-3α-tert-butyldimethylsilyloxy-7-(4-methoxycarbonyl-1-oxobutyl)-bicyclo[3,3,0]oct-6-ene, that is to say (±)-methyl (9S,11R),[mixture of 15R and 15S]-11,15-bis(tert-butyldimethylsiloxy-6,9-methano-5-oxo-prost-6,6a-en-13-ynoate [Mass spectrum m/e 547.3 (M+- tert-butyl); N.M.R. (in deuterochloroform): singlet at 3.6 ppm, multiplets at −0.1–0.1, 0.6–1.0, 1.0–1.6, 1.7–2.0, 2.0–2.4, 2.4–2.8, 3.1–3.3, 3.9–4.1, 4.1–4.3, 6.45–6.55 ppm].

REFERENCE EXAMPLE 3

A mixture (1:1 w/w) of 2β-(3-cyclohexyl-3α-tert-butyldimethylsilyloxyprop-1-ynyl)-3α-tert-butyldimethylsilyloxy-7-(4-methoxycarbonyl-1-oxobutyl)-bicyclo[3,3,0]oct-6-ene and 2α-(3-cyclohexyl-3α-tert-butyldimethylsilyloxyprop-1-ynyl)-3β-tert-butyldimethylsilyloxy-7-(4-methoxycarbonyl-1-oxobutyl)bicyclo-[3,3,0]oct-6-ene, that is to say methyl (9S,11R,15S)-11,15-bis(tert-butyldimethylsilyloxy)-15-cyclohexyl-6,9-methano-5-oxo-16,17,18,19,20-pentanorprost-6,6a-en-13-ynoate and its (9R,11S,15S)-diastereoisomer, (20 mg; prepared as described in Reference Example 1) was dissolved in hexanol (0.28 ml), treated with tetrakis(hexyloxy)titanium(IV) (12 mg) and stirred at 75° C. under argon for 16 hours. The mixture was then treated with hexane (10 ml) and dilute hydrochloric acid (1.0N; 5 ml). The organic layer was washed with aqueous sodium bicarbonate solution (5 ml) and then with saturated sodium chloride solution (10 ml), dried over anhydrous sodium sulphate and concentrated under reduced pressure, to give a crude oil (17 mg). This oil was subjected to medium pressure chromatography on a short column (30 cm × 1 cm) of silica gel, eluting with hexane (30 ml) and then with a mixture of ethyl acetate and hexane (1:19 v/v; 30 ml) followed by a mixture of ethyl acetate and hexane (1:9 v/v; 60 ml), to give a mixture (1:1 w/w) of 2β-(3-cyclohexyl-3α-tert-butyldimethylsilyloxyprop-1-ynyl)-3α-tert-butyldimethylsilyloxy-7-(4-hexyloxycarbonyl-1-oxobutyl)bicyclo[3,3,0]oct-6-ene and 2α-(3-cyclohexyl-3α-tert-butyldimethylsilyloxyprop-1-ynyl)-3β-tert-butyldi-methylsilyloxy-7-(4-hexyloxycarbonyl-1-oxobutyl)bi-cyclo[3,3,0]oct-6-ene, that is to say hexyl (9S,11R,15S)-11,15-bis(tert-butyldimethylsilyloxy)-15-cyclohexyl-6,9-methano-5-oxo-16,17,18,19,20-pentanorprost-6,6a-en-13-ynoate and its (9R,11S,15S)-diastereoisomer, (8.3 mg) [N.M.R. (in deutero-chloroform): singlets at 0.001, 0.002, 0.004, 0.007, multiplets at 0.7–2.0, 2.0–2.4, 2.4–2.8, 3.1–3.3, 3.9–4.1, 6.54 ppm].

By proceeding in a similar manner, but replacing the hexanol used as a starting material by the appropriate quantities of isopropanol and cyclohexanol respectively, there were prepared: a mixture (1:1 w/w) of 2β-(3-cyclohexyl-3α-tert-butyldimethylsilyloxyprop-1-ynyl)-3α-tert-butyldimethyl-silyloxy-7-(4-isopropoxycarbonyl-1-oxobutyl)bicyclo[3,3,0]oct-6-ene and 2α-(3-cyclohexyl-3α-tert-butyldimethylsilyloxyprop-1-ynyl)-3β-tert-butyldimethyl-silyloxy-7-(4-isopropoxycarbonyl-1-oxobutyl)bicyclo[3,3,0]oct-6-ene, that is to say isopropyl (9S,11R,15S)-11,15-bis(tert-butyldimethylsilyloxy)-15 -cyclohexyl-6,9-methano-5-oxo-16,17,18,19,20-pentanorprost-6,6a-en-13-ynoate and its (9R,11S,15S)-diastereo-isomer, N.M.R. (in deuterochloroform): four singlets at 0.0–0.,, multiple at 0.7–2.0, 2.0–2.4, 2.4–2.9, 3.1–3.3, 3.9–4.1, 4.86–5.04, 6.5–6.6 ppm]; and a mixture (1:1 w/w) of 2β-(3-cyclohexyl-3α-tert-butyldimethylsilyloxyprop-1-ynyl)-3α-tert-butyl-dimethylsilyloxy-7-(4-cyclohexyloxycarbonyl-1-oxo-butyl)-bicyclo[3,3,0]oct-6-ene and 2α-(3-cyclohexyl-3αtert-butyldimethylsilyloxyprop-1-ynyl)-3β-tert-butyl-dimethylsilyloxy-7-(4-cyclohexyloxycarbonyl-1-oxo-butyl)-bicyclo[3,3,0]oct-6-ene, that is to say cyclohexyl (9S,11S,15S)-11,15-bis(tert-butyldimethyl-silyloxy)-15-cyclohexyl-6,9-methano-5-oxo-16,17,18,19,20-pentanor-prost-6,6a-en-13-ynoate and its (9R,11S,15S)-diastereoisomer, [N.M.R. (in deuterochloroform): four singlets at 0.0–0.14, multiplets at 0.7–2.0, 2.0–2.4, 2.4–2.8, 3.1–3.3, 3.9–4.1, 4.6–4.8, 6.52 ppm].

The present invention includes within its scope pharmaceutical compositions which comprise at least one compound of the general formula shown in FIG. II or, when $R^1$ represents a hydrogen atom, a non-toxic salt thereof, or a cyclodextrin clathrate thereof, together with a pharmaceutical carrier or coating. In clinical practice the compounds of the formula shown in FIG. II will normally be administered orally, rectally, vaginally or parenterally.

Methods of presentation of pharmaceutically active compounds are well known in the art and a suitable vehicle may be determined by the physician, pharmacist or veterinarian, depending upon such factors as the effect sought, the size, age, sex and condition of the patient and, for veterinary uses, the species of the animal to be treated, and on the physical properties of the active compound. The compositions may also contain, as is usual in the art, such materials as solid or liquid diluents, wetting agents, preservatives, and flavouring and colouring agents.

Solid compositions for oral administration include compressed tablets, pills, dispersible powders, and granules. In such solid compositions one or more of the active compounds is, or are, admixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions, by irradiation, or by heating. They may also be manufactured in the form of sterile solid compositions, which can be dissolved in sterile water or some other sterile injectable medium immediately before use.

The compounds of the formula shown in FIG. II may alternatively be administered orally by any method known per se for administration by inhalation of drugs which are not themselves gaseous under normal conditions of administration. Thus, a solution of the active ingredient in a suitable pharmaceutically-acceptable solvent, for example water, can be nebulized by a mechanical nebulizer, for example a Wright Nebulizer, to give an aerosol of finely-divided liquid particles suitable for inhalation. The active ingredients may also be administered orally by inhalation in the form of aerosols generated from self-propelling pharmaceutical compositions.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment. In the adult, the doses are generally between 0.0002 and 2.0 mg/kg body weight. More particularly, in the human adult, each dose per person is generally between 0.02 and 100 mg in the treatment of hypertension, disorders of the peripheral circulation, cerebral ischaemia, myocardial infarction, arteriosclerosis, gastrointestinal bleeding induced by non-steroidal anti-inflammatory drugs, peptic ulceration and thromboses, especially by parenteral administration. If necessary these doses may be repeated as and when required.

The following Composition Example illustrates pharmaceutical compositions according to the invention.

COMPOSITION EXAMPLE

A mixture (1:1 w/w) of methyl (9S,11R,15S)-15-cyclohexyl-11,15-dihydroxy-6,9-methano-5-oxo-16,17,18,19,2019,20-pentanorprost-6,6a-en-13-ynoate and its (9R,11S,15S)-diastereoisomer (compound A) (0.5 mg) was dissolved in ethanol (5 ml). The solution was then sterilised by passage through a bacteria-retaining filter and placed in 0.1 ml portions in 1 ml ampoules, to give 0.01 mg of the mixture (1:1 w/w) of methyl (9S,11R,15S)-15-cyclohexyl-11,15-dihydroxy-6,9-methano-5-oxo-16,17,18,19,20-pentanorprost-6,6a-en-13-ynoate and its (9R,11S,15S)-diastereoisomer per ampoule. The ampoules were sealed. The contents of an ampoule diluted to a suitable volume with a suitable aqueous buffer solution gave a solution ready for administration by injection.

Similar compositions may be prepared by replacing compound A by the appropriate quantities of any others of compounds B to F hereinbefore identified.

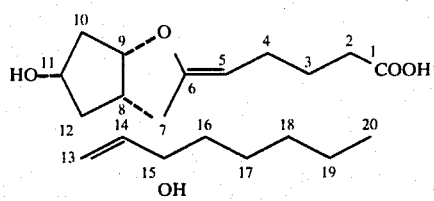

FIG. I

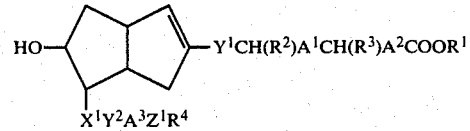

FIG. II

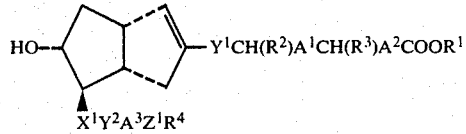

FIG. III

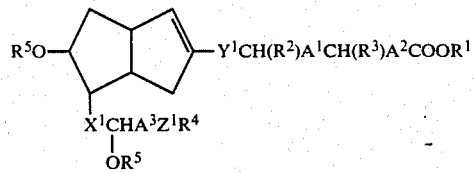

FIG. IV

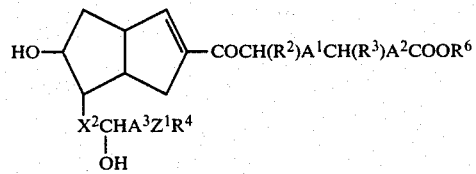

FIG. V

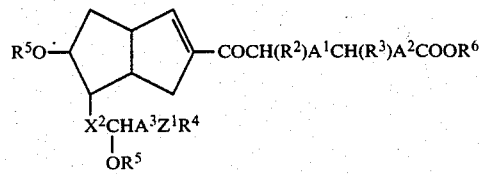

FIG. VI

We claim:
1. A prostaglandin analogue of the formula:

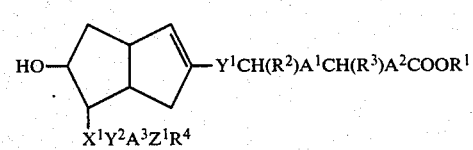

II (wherein $R^1$ represents a hydrogen atom or a straight-or branched-chain akyl group containing from 1 to 12 carbon atoms, optionally substituted by a cycloalkyl group containing from 3 to 8 carbon atoms, or a mono-, bi- or tri-cycloalkyl or mono-, bi- or tri-cycloalkenyl group containing up to 10 carbon atoms and optionally substituted by one or two straight- or branched-chain alkyl or alkenyl groups each containing up to 3 carbon atoms, $Y^1$ represents a carbonyl or hydroxymethylene group, $A^1$ represents an alkylene linkage containing 1, 2 or 3 carbon atoms and optionally bearing a methyl or ethyl substituent, $R^2$ represents a hydrogen atom or a methyl or ethyl group and $R^3$ represents a hydrogen atom or $R^2$ and $R^3$ form an alkylene linkage containing 2 or 3 carbon atoms, optionally bearing a methyl or ethyl substituent, such that the symbols $A^1$, $R^2$ and $R^3$, together with the carbon atoms through which they are connected, may form a cycloalkyl ring of 5, 6, 7 or 8 carbon atoms, optionally bearing one or two methyl or ethyl substituents, or $A^1$ and $R^3$, together with the carbon atom through which they are connected, may form a phenylene ring optionally substituted by a halogen atom or by a trifluoromethyl group or by a straight- or branched-chain alkyl or alkoxy group containing from 1 to 6 carbon atoms, $A^2$ represents a direct bond or a methylene group optionally bearing one or two methyl or ethyl substituents, $X^1$ represents an ethylene, trans-vinylene or ethynylene group, $Y^2$ represents a carbonyl or hydroxymethylene group, and either (i) $A^3$ represents a straight- or branched-alkylene chain containing from 1 to 5 carbon atoms, $Z^1$ represents a direct bond or an oxygen or sulphur atom, and $R^4$ represents a group $R^{4'}$ which is a straight- or branched-chain alkyl group containing from 1 to 12 carbon atoms, optionally substituted by a cycloalkyl group containing from 3 to 8 carbon atoms, or a mono-, bi-or tri-cycloalkyl or mono, bi- or tri-cycloalkenyl group containing up to 10 carbon atoms and optionally substituted by one or two straight- or branched-chain alkyl or alkenyl groups each contaning up to 3 carbon atoms, or $R^4$ represents a phenyl group optionally substituted by a halogen atom or by a trifluoromethyl group or by a straight- or branched-chain alkyl or alkoxy group containing from 1 to 6 carbon atoms, or (ii) $A^3$ and $Z^1$ both represent direct bonds and $R^4$ represents a group $R^{4'}$ as hereinbefore defined) or a cyclodextrin clathrate thereof or when $R^1$ represents a hydrogen atom a non-toxic salt thereof.

2. A prostaglandin analogue according to claim 1 wherein $R^1$ represents a hydrogen atom or a straight- or branched-chain alkyl group containing from 1 to 6 carbon atoms, optionally substituted by a cycloalkyl group containing from 3 to 8 carbon atoms, or a mono-, bi or tri-cycloalkyl or mono-, bi- or tri-cycloalkenyl group containing up to 10 carbon atoms and optionally substituted by one or two straight- or branched-chain alkyl or alkenyl groups each containing up to 3 carbon atoms.

3. A prostaglandin analogue according to claim 1 wherein the hydrogen atoms attached to the 8- and 9-positions are both in beta configuration.

4. A prostaglandin analogue according to claim 1 wherein the side-chain attached in the 12-position is cis with respect to the hydrogen atoms attached to the 8- and 9- positions.

5. A prostaglandin analogue according to claim 1 conforming to the general formula:

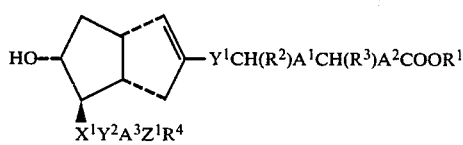

III (wherein the various symbols are as defined in claim 1) and the enantiomer thereof, and non-toxic salts and cyclodextrin clathrates thereof.

6. A prostaglandin analogue according to claim 1 wherein $A^1$ represents a methylene group.

7. A prostaglandin analogue according to claim 1 wherein $A^2$ represents a direct bond.

8. A prostaglandin analogue according to claim 1 wherein $A^3$ represents a direct bond.

9. A prostaglandin analogue according to claim 1 wherein $R^1$ represents an alkyl group containing from 1 to 6 carbon atoms or a cyclohexyl group.

10. A prostaglandin analogue according to claim 1 wherein $R^2$ represents a hydrogen atom.

11. A prostaglandin analogue according to claim 1 wherein $R^3$ represents a hydrogen atom.

12. A prostaglandin analogue according to claim 1 wherein $R^4$ represents an alkyl group containing from 1 to 5 carbon atoms or a cyclohexyl group.

13. A prostaglandin analogue according to claim 1 wherein $X^1$ represents an ethynylene group.

14. A prostaglandin analogue according to claim 1 wherein $Y^2$ represents a hydroxymethylene group.

15. A prostaglandin analogue according to claim 1 wherein $Z^1$ represents a direct bond.

16. A compound according to claim 1 which is methyl (9S,11R,15S)-15-cyclohexyl-11,15-dihydroxy-6,9-methano-5-oxo-16,17,18,19,20-pentanorprost-6,6a-en-13-ynoate and its (9R,11S,15S)-diastereoisomer.

17. A compound according to claim 1 which is (±)-methyl (9S,11R),(mixture of 15R and 15S)-11,15-dihydroxy-6,9-methano-5-oxoprost-6,6a-en-13-ynoate.

18. A compound according to claim 1 which is (±)-methyl (9S,11R),(mixture of 5R and 5S) (mixture of 15R and 15S)-5,11,15-trihydroxy-6,9-methanoprost-6,6a-en-13-ynoate.

19. A compound according to claim 1 which is hexyl (9S,11R,15S)-15-cyclohexyl-11,15-dihydroxy-6,9-methano-5-oxo-16,17,18,19,20-pentanorprost-6,6a-en-13-ynoate and its (9R,11S,15S)-diastereoisomer.

20. A compound according to claim 1 which is isopropyl (9S,11R,15S)-15-cyclohexyl-11,15-dihydroxy-6,9-methano-5-oxo-16,17,18,19,20-pentanorprost-6,6a-en 13-ynoate and its (9R,11S,15S)-diastereoisomer.

21. A compound according to claim 1 which is cyclohexyl (9S,11R,15S)-15-cyclohexyl-11,15-dihydroxy-6,9-methano-5-oxo-16,17,18,19,20-pentanorprost-6,6a-en-13-ynoate and its (9R,11S,15S)-diastereoisomer.

22. A pharmaceutical composition useful in the treatment of hypertension, disorders of the peripheral circulation, cerebral ischaemia, myocardial infarction, arteriosclerosis, gastrointestinal bleeding induced by non-steroidal anti-inflammatory drugs, peptic ulceration and thromboses, which comprises as active ingredient, an effective amount of a prostaglandin analogue as claimed in claim 1, or a cyclodextrin clathrate thereof or, when $R^1$ in formula II represents a hydrogen atom, a non-toxic salt thereof.

23. A method for the treatment of hypertension, disorders of the peripheral circulation, cerebral ischaemia, myocardial infarction, arteriosclerosis, gastrointestinal bleeding induced by non-steroidal anti-inflammatory drugs, peptic ulceration or thromboses in a host which comprises the administration of an effective amount of a prostaglandin analogue according to claim 1, or a cyclodextrin clathrate thereof or, when $R^1$ in formula II represents a hydrogen atom, a non-toxic salt thereof.

* * * * *